US008263704B2

(12) United States Patent
Stopek et al.

(10) Patent No.: US 8,263,704 B2
(45) Date of Patent: Sep. 11, 2012

(54) BIOABSORBABLE SURGICAL COMPOSITION

(75) Inventors: Joshua B. Stopek, Yalesville, CT (US); Ahmad Robert Hadba, Wallingford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 686 days.

(21) Appl. No.: 12/409,642

(22) Filed: Mar. 24, 2009

(65) Prior Publication Data

US 2009/0266467 A1  Oct. 29, 2009

Related U.S. Application Data

(60) Provisional application No. 61/047,122, filed on Apr. 23, 2008.

(51) Int. Cl.
A61K 47/48 (2006.01)
(52) U.S. Cl. ........ 525/54.2; 525/410; 525/411; 525/415; 525/450; 525/403; 528/354; 528/361; 528/403
(58) Field of Classification Search ................. 525/54.2, 525/410, 411, 415, 450, 403; 528/354, 361, 528/403
See application file for complete search history.

(56) References Cited

U.S. PATENT DOCUMENTS

| | | | |
|---|---|---|---|
| 3,631,138 | A | 12/1971 | Peters |
| 4,061,662 | A | 12/1977 | Marans et al. |
| 4,169,175 | A | 9/1979 | Marans et al. |
| 4,359,049 | A | 11/1982 | Redl et al. |
| 4,361,055 | A | 11/1982 | Kinson |
| 4,743,632 | A | 5/1988 | Marinovic |
| 4,874,368 | A | 10/1989 | Miller et al. |
| 4,954,593 | A | 9/1990 | Vara et al. |
| 4,978,336 | A | 12/1990 | Capozzi et al. |
| 4,979,942 | A | 12/1990 | Wolf et al. |
| 5,368,563 | A | 11/1994 | Lonneman et al. |
| 5,510,121 | A | 4/1996 | Rhee et al. |
| 5,703,158 | A | 12/1997 | Duan et al. |
| 6,201,065 | B1 | 3/2001 | Pathak et al. |
| 6,211,249 | B1 * | 4/2001 | Cohn et al. ........... 514/772.1 |
| 6,527,749 | B1 | 3/2003 | Roby et al. |
| 6,566,406 | B1 | 5/2003 | Pathak et al. |
| 6,653,423 | B1 | 11/2003 | Yamamoto et al. |
| 6,706,260 | B1 | 3/2004 | Tanaka et al. |
| 6,818,018 | B1 | 11/2004 | Sawhney |
| 7,009,034 | B2 | 3/2006 | Pathak et al. |
| 7,025,990 | B2 | 4/2006 | Sawhney |
| 7,202,325 | B2 | 4/2007 | Pacetti et al. |
| 7,211,651 | B2 | 5/2007 | Pathak |
| 7,332,566 | B2 | 2/2008 | Pathak et al. |
| 2003/0157193 | A1 | 8/2003 | McDonald et al. |
| 2004/0092695 | A1 | 5/2004 | Hu et al. |
| 2005/0142162 | A1 | 6/2005 | Hunter et al. |
| 2005/0175667 | A1 | 8/2005 | Carlyle |
| 2006/0193884 | A1 | 8/2006 | Stopek et al. |
| 2007/0032666 | A1 | 2/2007 | Read et al. |
| 2007/0128152 | A1 | 6/2007 | Hadba et al. |
| 2007/0135605 | A1 | 6/2007 | Hadba et al. |
| 2007/0135606 | A1 | 6/2007 | Belcheva et al. |
| 2008/0033106 | A1 | 2/2008 | Koroskenyl et al. |
| 2009/0048423 | A1 | 2/2009 | Stopek |

FOREIGN PATENT DOCUMENTS

| | | |
|---|---|---|
| EP | 1 719 530 A | 11/2006 |
| EP | 1857489 A1 | 11/2007 |
| GB | 985 144 | 3/1965 |
| GB | 1 143 309 | 2/1969 |
| GB | 1 187 362 | 4/1970 |
| GB | 2408510 | 6/2005 |
| WO | WO 92/22599 A1 | 12/1992 |
| WO | WO 01/00246 A | 1/2001 |
| WO | WO 01/16210 A | 3/2001 |
| WO | WO 02/056790 A2 | 7/2002 |
| WO | WO 2005/032461 A2 | 4/2005 |
| WO | WO 2005/099768 A2 | 10/2005 |
| WO | WO 2005/100429 A1 | 10/2005 |
| WO | WO 2006/010278 A1 | 2/2006 |
| WO | WO 2006/084911 A2 | 8/2006 |
| WO | WO 2006/107957 A2 | 10/2006 |
| WO | WO 2006/128742 A2 | 12/2006 |
| WO | WO 2006/128918 A1 | 12/2006 |
| WO | WO 2007/001448 A2 | 1/2007 |
| WO | WO 2007/067623 A | 6/2007 |
| WO | WO 2007/133782 A1 | 11/2007 |
| WO | WO 2008/047100 A1 | 4/2008 |

OTHER PUBLICATIONS

European Search Report for EP 09251137-7-1214 date of completion is Sep. 2, 2009 (3 pages).
Tom, B. et al., "Bradykinin potentiation by ACE inhibitors: a matter of metabolism", *British Journal of Pharmacology* vol. 137, pp. 276-284 (2002).
Iwasaki, Y., et al., "In vitro and ex vivo blood compatibility study of 2-methacryloyloxyethyl phosphorylcholine (MPC) copolymer-coated hemodialysis hollow fibers", *J. Artif Organs*, vol. 6, pp. 260-266 (2003).
Nakabayashi, N., et al., "Copolymers of 2-methacryloyloxyethyl phosphorylcholine (MPC) as biomaterials", *Bio-Medical Materials and Engineering*, vol. 14, pp. 345-354 (2004).
PCT International Search Report from Application No. PCT/US07/26003 dated Apr. 16, 2008.
PCT International Search Report from Application No. PCT/US08/63147 dated Aug. 4, 2008.

(Continued)

*Primary Examiner* — David W Wu
*Assistant Examiner* — Robert Jones, Jr.

(57) ABSTRACT

Bioabsorbable macromer compositions are provided including a polymeric component possessing a lipid segment which enhances the affinity of the macromer composition to targeted tissue. In some embodiments, the polymeric component can be combined with a second component. The resulting bioabsorbable macromer composition can be employed as an adhesive or sealant for medical/surgical uses.

19 Claims, No Drawings

OTHER PUBLICATIONS

PCT International Search Report from Application No. PCT/US08/63149 dated Aug. 11, 2008.
PCT International Search Report from Application No. PCT/US08/63571 dated Aug. 15, 2008.
International Search Report from European Application No. EP 06 84 4894 date of completion Jun. 9, 2010.
International Search Report from European Application No. EP 06 84 4890 date of completion Jun. 4, 2010.
Ferreira, et al., "Modification of the Biopolymer Castor Oil With Free Isocyanate Groups to be Applied As Bioadhesive", *International Journal of Biological Macromolecules*, vol. 40, No. 2, pp. 144-152 (2007).
Ferreira, et al., "Development of a Biodegradable Bioadhesive Containing Urethane Groups", *Journal of Materials Science: Materials in Medicine*, vol. 19, No. 1, pp. 111-120 (2007).
International Search Report from European Application No. EP 08 25 3645 mailed Mar. 5, 2009.
European Search Report for Appln. No. EP 08 25 3647 completed Mar. 6, 2009.
European Search Report for Appln. No. EP 08 25 1790.5 completed Jun. 19, 2009.

* cited by examiner

BIOABSORBABLE SURGICAL COMPOSITION

CROSS-REFERENCE TO RELATED APPLICATIONS

This application claims the benefit of and priority to U.S. Provisional Patent Application No. 61/047,122, filed Apr. 23, 2008, the entire disclosure of which is incorporated by reference herein.

TECHNICAL FIELD

The present disclosure relates to compositions suitable for application in situ, including for use as tissue adhesives and/or tissue sealants.

DESCRIPTION OF THE RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high flexural modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

It would be desirable to provide a biological adhesive that is highly consistent in its properties without the concern of viral transmission. Such a composition should be flexible and biocompatible and should be suitable for use as an adhesive or sealant.

SUMMARY

The present disclosure provides biological compositions suitable for use as tissue adhesives and/or sealants. In embodiments, a bioabsorbable macromer composition of the present disclosure may be of the formula $$R_1\text{-}[A]_v\text{-}R_2 \qquad (II)$$

or $$R_2\text{-}[A]_v\text{-}R_1\text{-}[A]_v\text{-}R_2 \qquad (III)$$

wherein $R_1$ includes a lipid segment, $R_2$ includes a polymer segment such as a polysaccharide or polyol, A is a bioabsorbable group, and v is a number from about 1 to about 20.

In other embodiments, a bioabsorbable macromer composition of the present disclosure may be of the formula $$R_1\text{-}[A]_v\text{-}R_2\text{—}R_3 \qquad (IV)$$

or $$R_3\text{—}R_2\text{-}[A]_v\text{-}R_1\text{-}[A]_v\text{-}R_2\text{—}R_3 \qquad (V)$$

wherein $R_1$ includes a lipid segment, $R_2$ includes a polymer such as a polysaccharide or a polyol, $R_3$ includes a functional component such as isocyanates, succinimides, aldehydes, and combinations thereof, A is a bioabsorbable group, and v is a number from about 1 to about 20.

In yet other embodiments, a bioabsorbable macromer composition of the present disclosure may include a polymeric component of the formula $$R_3\text{—}R_2\text{-}[A]_v\text{-}R_1\text{-}[A]_v\text{-}R_2\text{—}R_3 \qquad (V)$$

wherein $R_1$ includes a lipid segment, $R_2$ includes a polymer such as a polysaccharide or polyol, $R_3$ includes a functional component such as isocyanates, succinimides, aldehydes, and combinations thereof, A is a bioabsorbable group, and v is a number from about 1 to about 20, and a second component possessing at least one group reactive with the functional component on the polymeric compound. In embodiments the functional component on the polymeric compound may be an isocyanate, in which case the second component may possess at least one isocyanate-reactive group such as at least one hydroxy group, at least one amine group, at least one sulfhydryl group, and combinations thereof.

Methods for using the compositions of the present disclosure are also provided. In embodiments, methods for closing wounds are provided which include applying the bioabsorbable macromer compositions of the present disclosure to a wound, and allowing the bioabsorbable macromer composition to set, thereby closing the wound. In embodiments, the wound to be closed may be a surgical incision.

The bioabsorbable macromer compositions of the present disclosure may also be used to fill a void in animal tissue by applying the composition to the void and allowing the composition to set, thereby filling the void.

Compositions of the present disclosure may also be used to adhere medical devices, such as implants, to the surface of animal tissue. In embodiments, a method for adhering a medical device to tissue may include applying the bioabsorbable macromer composition of the present disclosure to the device, the tissue surface or both, bringing the device, bioabsorbable macromer composition and surface into contact with each other, and allowing the bioabsorbable macromer composition to set thereby adhering the device and tissue surface to each other.

DETAILED DESCRIPTION

The present disclosure relates to a macromer composition for use as a tissue adhesive or sealant, which is biocompatible, non-immunogenic and biodegradable. The bioabsorbable macromer composition can be applied to living tissue and/or flesh of animals, including humans. The bioabsorbable macromer composition can be employed to adhere tissue edges, seal air/fluid leaks in tissues, adhere medical devices, i.e. implants, to tissue, and for tissue augmentation such as sealing or filling voids or defects in tissue. The composition may also be utilized as a tissue protective coating, an anti-adhesive coating, a drug delivery vehicle, and the like.

While certain distinctions may be drawn between the usage of the terms "flesh" and "tissue" within the scientific community, the terms are used interchangeably herein as referring to a general substrate upon which those skilled in the art would understand the present bioabsorbable macromer composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic and/or ascite tissue.

The composition of the present disclosure includes a polymeric component possessing a lipid, phospholipid, or lipid-like segment in combination with a polymer segment, which may be a polymer, oligomer, and/or macromer. As used herein, "lipid", and "lipid-like" may be utilized interchangeably to refer to a substance such as a fat, oil or wax that is hydrophobic in nature, for example, it dissolves in alcohol but not in water. As used herein, a "polymer segment" may include a polymer, oligomer, and/or macromer. As used herein, an oligomer may include repeating monomeric units of from about 4 units to about 50 units, in embodiments from about 5 units to about 20 units. A macromer of the present disclosure is of a longer length, of from about 50 units to about 500 units, in embodiments from about 75 units to about 200 units. A polymer of the present disclosure is of a longer length of from about 500 units to about 20,000 units, in embodiments from about 750 units to about 10,000 units.

The lipid-like segment may improve the tissue wetting or penetration properties of the composition. The lipid segment, the polymer segment, or both, may be conjugated to biomolecules including proteins, peptides, polysaccharides, synthetic polymers or oligomers, alkylene oxides, polymer drugs, composites including the foregoing, combinations thereof, and the like, utilizing methods within the purview of those skilled in the art.

Suitable lipid segments which may be utilized in forming compositions of the present disclosure include, but are not limited to, lipids, phospholipids and/or phospholipid derivatives. Examples of such lipid segments include, but are not limited to, phosphoryl choline, phosphatidyl choline, phosphatidyl ethanolamine, phosphatidyl inositol, phosphatidyl glycerol, phosphatidyl serine, phosphatidic acid, lysophosphatidyl choline, lysophosphatidyl ethanolamine, lysophosphatidyl glycerol, lysophosphatidyl serine, lysophosphatidic acid, polyethylene glycol (PEG)-phosphatidylethanolamine, polyvinyl pyrrolidone (PVP)-phosphatidylethanolamine, sphingosine, aminosphingosine, combinations thereof, and the like.

In other embodiments, the lipid segment may include fatty acids, randomly spaced hydrophilic/hydrophobic vinyl monomers including acrylates, methacrylates, phosphorylcholine-containing polymers, combinations thereof, and the like.

Suitable phosphorylcholine-containing polymers are within the purview of those skilled in the art and include, for example, phosphorylcholines derived from monomers such as 2-methacryloyloxyethyl phosphorylcholine (MPC) including MPC-co-butyl acrylate, MPC-co-hydroxyethyl methacrylate, 2-acryloyloxyethyl phosphorylcholine, combinations thereof, and the like. Other phosphorylcholines may be utilized, including phosphorylcholines based upon monomers including, but not limited to, 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butyl phosphate, and combinations thereof. As used herein, "(meth)acryl" includes both methacryl and/or acryl groups. Methods for forming phosphorylcholines from such monomers are within the purview of those skilled in the art.

In embodiments, a suitable polymer segment may include anionic polysaccharides such as carboxymethyl cellulose (CMC), alginate, chitosan and hyaluronic acid; proteins including gelatin, collagen and albumin; polypeptides including poly(glutamic) acid, poly(lysine), and copolymers of multiple amino acids; polyols including polyalkylene oxides, polyvinyl alcohols, combinations thereof, and the like; copolymers of polyalkylene oxides such as polyethylene glycol with degradable polymers prepared from L-lactide, DL-lactide, glycolide, ε-caprolactone, p-dioxanone, trimethylene carbonate, combinations thereof, and the like. Combinations of any of the foregoing may be utilized in embodiments.

In other embodiments, UV polymerizable or curable oligomers, macromers, or polymers may be utilized as the polymer segment, including acrylates such as polyethylene glycol acrylate, polyethylene glycol diacrylate, polyethylene glycol fumarate, polycaprolactone fumarate, polyglycolide fumarate, polylactide fumarate, copolymers thereof, combinations thereof, and the like.

In some embodiments, the polymer segment can be a polyol such as a polyalkylene oxide including polyethylene oxide ("PEO"), polypropylene oxide ("PPO"), polyethylene glycol ("PEG"), polypropylene glycol ("PPG"), a polyethylene glycol with lactide linkages, polyethylene glycol-adipate, co-polyethylene oxide block or random copolymers, polyethylene glycol-polypropylene glycol copolymers including poloxamers such as polyethylene oxide (PEO) copolymers with polypropylene oxide (PPO) such as the triblock PEO-PPO copolymers commercially available as PLURONICS® from BASF Corporation (Mt. Olive, N.J.), combinations thereof, and the like.

In embodiments a polyalkylene oxide may be utilized as the polymer, such as a polyethylene oxide, such as a polyethylene glycol ("PEG"). As used herein, polyethylene glycol generally refers to a polymer with a molecular weight of less than 50,000, while polyethylene oxide is used for higher molecular weights. PEGs provide excellent water retention, flexibility and viscosity in the biocompatible synthetic macromer composition.

In embodiments, a PEG may be utilized as the polymer segment having a molecular weight of from about 100 to about 20,000, in embodiments from about 500 to about 10,000, in other embodiments from about 1,000 to about 5,000.

succinic acid, glutaric acid, adipic acid, sebacic acid, azelaic acid, combinations thereof, and the like, to produce a component having carboxylic acid functionality. The component having carboxylic functionality may then be reacted with an amine such as 4-(p-azidosalicylamido-butylamine (ASBA) in combination with a carbodiimide such as EDC (1-ethyl-3 (3-dimethyl-amino propyl)-carbodiimide hydrochloride). An overview of the reaction is as follows:

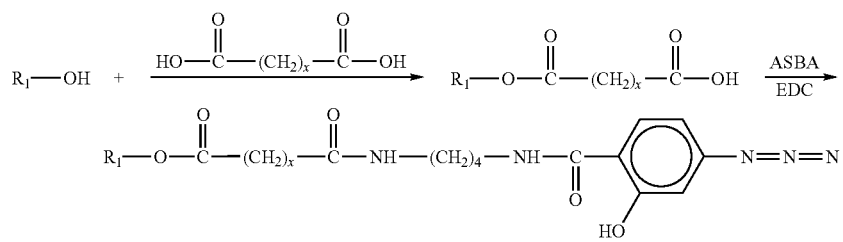

In embodiments, the composition of the present disclosure, including the lipid segment and polymer segment described above, may include bioabsorbable groups. Bioabsorbable groups are within the purview of those skilled in the art and can include those which undergo hydrolytic degradation. Suitable bioabsorbable groups include hydrolytically labile α-hydroxy acids such as lactic acid and glycolic acid, glycolide, lactide, lactones including ε-caprolactone, carbonates such as trimethylene carbonate, ester ethers such as dioxanones including 1,4-dioxane-2-one and 1,3-dioxane-2-one, diacids including succinnic acid, adipic acid, sebacic acid, malonic acid, glutaric acid, azelaic acid, phosphoesters such as ethyl dichlorophosphate, anhydrides such as sebacic acid anhydride and azelaic acid anhydride, etc., and combinations thereof.

Methods for introducing these bioabsorbable groups into the lipid segment and/or polymer segment are within the purview of those skilled in the art. For example, a bioabsorbable group may be incorporated by first reacting the lipid segment with a polyhydric alcohol such as D-sorbitol, D-mannitol, tris(hydroxymethyl)aminomethane (also known as 2-amino-2-(hydroxymethyl)-1,3-propanediol), diethylene glycol, threitol, pentaerythritol, enterodiol, cyclodextrins, etc. to form a lipid segment having multiple hydroxy groups, i.e., $$R_1-(OH)_n \qquad (I)$$

where $R_1$ is the lipid segment, and n is a number from about 1 to about 20. For example, in embodiments, $R_1$ may be a phosphorylcholine functional oligomer, for example MPC-co-hydroxyethyl methacrylate.

The lipid segment having multiple hydroxy groups may then, in turn, be reacted with a hydroxy acid such as lactic acid, glycolic acid, or other bioabsorbable groups as described above, including lactones, to form a lipid segment having multiple bioabsorbable/hydroxy groups.

The polymer segment described above may then be reacted with the bioabsorbable group to form a polymeric composition including the lipid segment, the bioabsorbable group, and the polymer segment.

Methods for reacting the polymer segment with the lipid segment, optionally possessing bioabsorbable groups, are within the purview of those skilled in the art. For example, in some embodiments, a lipid segment having hydroxyl functionality may be reacted with a diacid such as malonic acid, wherein $R_1$ is as defined above and x may be from about 1 to about 20.

The resulting polymer may then be subjected to polymerization, such as UV polymerization, to produce a composition of the present disclosure that does not possess any functionality on its ends.

In other embodiments, a reaction scheme similar to the above may be utilized to form a polymeric component of the following formulas $$R_1\text{-}[A]_v\text{-}R_2 \qquad (II)$$

or $$R_2\text{-}[A]_v\text{-}R_1\text{-}[A]_v\text{-}R_2 \qquad (III)$$

wherein $R_1$ is the lipid segment, $R_2$ is the polymer segment, i.e., an oligomer, macromer or polymer as described above, A is a bioabsorbable group as described above, and v is a number from about 1 to about 20, in embodiments from about 2 to about 6. In embodiments, $R_1$ may be a phospholipid such as phosphatidylcholine, $R_2$ may be a polyalkylene oxide such as a polyethylene glycol or a polyethylene glycol/polypropylene glycol copolymer, and A may be lactide, glycolide, ε-caprolactone, trimethylene carbonate, p-dioxanone, combinations thereof, and the like, as well as a diacid such as malonic acid, succinic acid, glutaric acid, adipic acid, sebacic acid, azelaic acid, combinations thereof, and the like.

In addition, terminal lipid or polymer segments may be functionalized with bioreactive groups targeted for binding and/or bonding to tissue to function as adhesives, either by covalent, ionic, hydrogen, electrostatic, combinations thereof, and the like. For example, in embodiments, a terminal lipid segment or a terminal polymer segment may be functionalized with a group capable of reacting with amines native to tissue, thereby bonding the composition of the present disclosure to the tissue to which it is applied. Suitable groups for such bonding include, but are not limited to, isocyanates, ketones, aldehydes, succinimides, epoxides, carboxylic acids, combinations thereof, and the like.

For example, the polymer with lipid segments can be end-capped with isocyanates and/or succinimides. As used herein, succinimides also include sulfosuccinimides, succinimide esters and sulfosuccinimide esters, including N-hydroxysuccinimide ("NHS"), N-hydroxysulfosuccinimide ("SNHS"), N-hydroxyethoxylated succinimide ("ENHS"), N-hydroxysuccinimide acrylate, succinimidyl glutarate, n-hydroxysuccinimide hydroxybutyrate, combinations thereof, and the like. In embodiments, the functional group utilized for endcapping may be any functional group as described in U.S. Pat. Nos. 6,566,406, 6,818,018, 7,009,034, 7,025,990, 7,211,651, 7,332,566, the entire disclosures of each of which are incorporated by reference herein, and may be combined with the other components of the polymeric component possessing a lipid segment utilizing any method within the purview of those skilled in the art, including those disclosed in U.S. Pat. Nos. 6,566,406, 6,818,018, 7,009,034, 7,025,990, 7,211,651, and/or 7,332,566, the entire disclosures of each of which are incorporated by reference herein.

In other embodiments, for example, an isocyanate group (NCO) may be reacted with the lipid segment so that the terminal end of the polymer segment possesses isocyanate groups or, in embodiments, isocyanates may be utilized for endcapping the polymer segment possessing lipid segments as described above. Examples of suitable isocyanates for endcapping the polymer segment with lipid segments include, but are not limited to, aromatic, aliphatic and alicyclic isocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science. Combinations of the foregoing may be utilized in embodiments. In embodiments, an aliphatic diisocyanate such as hexamethylene diisocyanate can be used.

The resulting endcapped bioabsorbable polymeric component can be linear or can have a branched or star configuration. The molecular weight of the polymeric component can be from about 100 to about 20,000, in embodiments from about 300 to about 10,000, in other embodiments from about 500 to about 5000.

In some embodiments, the endcapped polymeric component with lipid segments can be of the formulas

$$R_1-[A]_v-R_2-R_3 \quad (IV)$$

or

$$R_3-R_2-[A]_v-R_1-[A]_v-R_2-R_3 \quad (V)$$

wherein $R_1$ is the lipid segment, $R_2$ is an oligomer, macromer or polymer as described above, A is a bioabsorbable group, v is a number from about 1 to about 20, in embodiments from about 2 to about 6, and $R_3$ is a functional group utilized to endcap the polymer, including an isocyanate, in embodiments a diisocyanate as described above, as well as succinimides, sulfosuccinimides, succinimide esters and sulfosuccinimide esters, including N-hydroxysuccinimide ("NHS"), N-hydroxysulfosuccinimide ("SNHS"), N-hydroxyethoxylated succinimide ("ENHS"), N-hydroxysuccinimide acrylate, succinimidyl glutarate, n-hydroxysuccinimide hydroxybutyrate, aldehydes, combinations thereof, and the like.

The bioabsorbable groups can be present in the composition in amounts from about 5% to about 50% by weight of the composition of the present disclosure, in embodiments from about 10% to about 40% by weight of the composition of the present disclosure, in other embodiments from about 15% to about 30% by weight of the composition of the present disclosure.

In addition to components that provide bioabsorbable groups, at least one linkage that is enzymatically degradable may be incorporated into the polymeric component. Linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln(Arg)$_2$-, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Those skilled in the art will readily envision reaction schemes for incorporating enzymatically degradable linkages into the polymeric component.

Synthetic lipid segments utilized in forming the compositions of the present disclosure may be synthesized so that they possess specific solubilities in various tissue sites, including major organ systems such as the gastrointestinal tract, lungs, liver, kidneys, bladder, and the like. For example, by adding a phosphatidylcholine lipid segment including randomly spaced hydrophilic/hydrophobic acrylic or vinyl monomers such as hydroxyethyl methacrylate or n-butyl methacrylate as described above, as well as vinyl compounds functionalized with quaternary ammoniums, potassium sulfopropyl acrylate (KSPA), n-vinyl pyrrolidone, acrylic acid, and the like, optionally in combination with an additional polymer segment, the solubility in various tissues may be enhanced.

The polymeric component possessing lipid segments and polymer segments of the present disclosure can be utilized by itself or, in embodiments, combined with a second component to form a bioabsorbable macromer composition of the present disclosure which may be useful as an adhesive or sealant. For example, where the polymeric component possessing a lipid segment has been endcapped with isocyanate groups, the second component of the present disclosure can possess at least one isocyanate-reactive group. In embodiments, suitable isocyanate-reactive groups may be at least one hydroxy group, at least one amine group, at least one sulfhydryl group, combinations thereof, and the like. Similarly, where the polymeric component has been functionalized with succinimides, sulfosuccinimides, n-hydroxysuccinimides, n-hydroxysulfosuccinimides, esters thereof (sometimes referred to herein as "succinimide-like groups") and the like, the second component may have groups reactive with the succinimide-like groups, including amines.

In embodiments, the second component may be selected so that it may be functionalized with appropriate groups for reacting with the polymeric component possessing a lipid-like segment. Suitable components for use as the second component may possess at least one hydroxy groups, at least one amine group, at least one sulfhydryl group, combinations thereof, and the like.

Suitable compounds possessing at least one hydroxy group which may be utilized as the second component include water and polyols such as polyether-based polyols, polycaprolactone-based polyols, and polyhydric alcohols such as glycerol, trimethylol propane, hexane-1,2,6-triol, pentaerythritol, glucose, mannitol, disaccharides such as sucrose, sorbitol and diethylene glycol.

Suitable components possessing at least one amine group which may be utilized as the second component are within the purview of those skilled in the art and include, for example, primary amines such as bis(3-aminopropyl)amine, spermine, polyetheramine (including JEFFAMINE® polyetheramines), and trilysine, as well as low molecular weight diamines, such as ethylenediamine, N-ethylethylenediamine and N,N'-diethylethylenediamine, butane-1,4-diamine, pentane-1,5-diamine, hexane-1,6-diamine, phenylene diamine, and combinations thereof. In other embodiments, alkanolamines may be utilized. Examples of suitable alkanolamines include dihydric and trihydric alkanolamines, such as ethanolamine and N-ethylethanolamine. Other amines which may be utilized include triethylenediamine, N-methylmorpholine, pentamethyl diethylenetriamine, dimethylcyclohexylamine, tetramethylethylenediamine, 1-methyl-4-dimethylaminoethyl-piperazine, 3-methoxy-N-dimethyl-propylamine, N-ethylmorpholine, diethylethanolamine, N-cocomorpholine, N,N-dimethyl-N',N'-dimethylisopropyl-propylene diamine, N,N-diethyl-3-diethyl aminopropylamine, and dimethyl-benzyl amine. Polymeric amines which may be utilized as the second component include polylysine, polyarginine, albumin, polyallylamine, MPC-co-acrylamide, MPC-co-polyallylamine, combinations thereof, and the like. In embodiments the amine utilized as the second component may be a diamine of the formula $$NH_2-R_4-NH_2 \qquad (VI)$$

wherein $R_4$ may be a polymer including any polymer segment described above, including polysaccharides, polyols, combinations thereof, and the like. In embodiments, $R_4$ may be a polyalkylene oxide such as polyethylene glycol, polypropylene glycol, copolymers of polyethylene glycol and polypropylene glycol, optionally containing any bioabsorbable groups as described above.

Combinations of any of the foregoing amines may be utilized in embodiments.

Suitable compounds possessing at least one sulfhydryl group which may be used as the second component include, but are not limited to, thiolated gelatin, thiolated collagen, PEG-thiols, pentaerythritol tetrakis(2-mercaptoacetate), pentaerythritol tetrakis(3-mercaptopropionate), trimethylolpropane tris(2-mercaptoacetate), trimethylolpropane tris(2-mercaptopropionate), combinations thereof, and the like.

In embodiments, the polymeric component possessing a lipid-like segment, the second component, or both, may be in a dilute solution. Suitable solvents which may be utilized to form a dilute solution include any biocompatible solvents within the purview of those skilled in the art which will not interfere with the reaction of the isocyanate-reactive groups of the second component with the isocyanate-functional groups of the polymeric component. Suitable solvents which may be utilized include, for example, polar solvents such as water, ethanol, triethylene glycol, dimethyl sulfoxide (DMSO), glymes (such as diglyme, triglyme, tetraglyme, and the like), polyethylene glycols, methoxy-polyethylene glycols, dimethylformamide, dimethylacetamide, gamma-butyrolactone, N-methylpyrollidone (NMP), ketones such as methyl ethyl ketone, cyclohexanone, diethylene glycol monoethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution.

A solvent may be mixed with the polymeric component, the second component, or both. A solvent may be mixed with the polymeric component so that the polymeric component is at a concentration of from about 1 weight percent to about 90 weight percent of the first solution, in embodiments from about 5 weight percent to about 40 weight percent of the first solution. A solvent may be mixed with the second component so that the second component is at a concentration of from about 1 weight percent to about 90 weight percent of the second solution, in embodiments from about 5 weight percent to about 40 weight percent of the second solution.

The amount of solvent used will depend on a number of factors including the particular polymeric component, second component, or both, that are to be employed and the intended end use of the composition.

The mixture of either the polymeric component possessing a lipid-like segment or second component and solvent as described herein may result in an emulsion or a diluted solution. The viscosity of the resulting emulsion or solution may be from about 100 cP to about 100,000 cP, in other embodiments from about 1,000 cP to about 80,00 cP, in still other embodiments from about 5,000 cP to about 20,000 cP.

In embodiments, the second component may be mixed with the polymeric component possessing a lipid-like segment at a ratio of from about 1:10 to about 10:1 by weight, in embodiments, at a ratio of from about 5:1 to about 1:1 by weight.

Where utilized, the second component may be present in the composition of the present disclosure in amounts from about 5% to about 90% by weight of the macromer composition, in embodiments from about 10% to about 80% by weight of the macromer composition, in other embodiments from about 15% to about 50% by weight of the macromer composition.

The concentrations of the polymeric component and the second component will vary depending upon a number of factors, including the types and molecular weights of the particular polymers used and the desired end use application, i.e., as an adhesive or sealant.

Where utilized alone, the polymeric component possessing a lipid-like segment can cross-link in situ to form a biocompatible adhesive or sealant. Where combined with the second component described above, the two components cross-link in situ when mixed together to form a biocompatible macromer composition suitable for use as an adhesive or sealant. The polymeric component possessing a lipid-like segment, optionally in combination with the second component, rapidly forms a three dimensional gel-like adhesive matrix, which reduces total surgical/operating time during a medical procedure.

The resulting bioabsorbable macromer compositions can be used in a medical/surgical capacity in place of, or in combination with, sutures, staples, clamps and the like. In embodiments, the bioabsorbable macromer compositions can be used to seal or adhere delicate tissue together, such as lung tissue, in place of conventional tools that may cause mechanical stress. The resulting bioabsorbable macromer compositions can also be used to seal air and/or fluid leaks in tissue as well as to prevent post-surgical adhesions and to fill voids and/or defects in tissue.

The bioabsorbable macromer compositions of the present disclosure can also act as drug carriers, allowing controlled release and direct delivery of a drug to a specific location in an animal, especially a human.

Where the polymeric component possessing a lipid-like segment is used alone to form the bioabsorbable macromer composition of the present disclosure, the polymeric component possessing a lipid-like segment and optional isocyanate groups can be exposed to water, optionally in the presence of a catalyst, to form a bioabsorbable macromer composition of the present disclosure. In embodiments, foaming agents may be added, for example carbonates including sodium bicarbonate, optionally in combination with an organic acid such as citric acid. In other embodiments, initiators may be included.

In embodiments, the bioabsorbable macromer composition may be prepared by combining the polymeric component possessing a lipid-like segment with the second component to form a three-dimensional crosslinked matrix. Cross-linking may be performed by exposing the components to water in the presence or absence of a catalyst, such as a tertiary amine catalyst. Suitable catalysts for use in the cross-linking reaction include 1,4-diazobicyclo[2.2.2]octane, triethylamine, diethylaminoethanol, dimethylamino pyridine, stannous octoate, etc. The amount of catalyst employed can be from about 0.5 grams to about 50 grams per kilogram of the components being cross-linked, in embodiments from about 1 gram to about 10 grams per kilogram of the components being cross-linked.

The exact reaction conditions for achieving cross-linking of the polymeric component possessing a lipid-like segment, optionally in combination with the second component, can vary depending on a number of factors such as the composition of the polymer, the degree of endcapping with additional functional groups such as isocyanates, the specific isocyanate utilized, and the desired degree of cross-linking. The cross-linking reaction may be conducted at temperatures from about 20° C. to about 40° C., in embodiments from about 25° C. to about 35° C., for a period of time from about 5 minutes to about 72 hours or more, in embodiments from about 1 hour to about 36 hours.

For the bioabsorbable macromer composition of the present disclosure, the use of higher concentrations of the polymeric component and optional second component may result in the formation of a more tightly crosslinked bioabsorbable macromer composition, producing a stiffer and stronger gel matrix. As such, bioabsorbable macromer compositions of the present disclosure intended for use in tissue augmentation may use higher concentrations of the polymeric and optional second components. Bioabsorbable macromer compositions of the present disclosure intended for use as bioadhesives or for the prevention of post-surgical adhesions need not be as firm and may therefore contain lower concentrations of the components.

Biologically active agents may be included in the bioabsorbable macromer compositions of the present disclosure. For example, naturally occurring polymers, including proteins such as collagen and derivatives of various naturally occurring polysaccharides such as glycosaminoglycans, can be utilized in forming the polymeric component possessing a lipid-like segment or incorporated into the bioabsorbable macromer compositions of the present disclosure. When these other biologically active agents also contain functional groups, the groups may react with functional groups on the polymeric and/or optional second components of the bioabsorbable macromer compositions of the present disclosure.

A variety of optional ingredients including medicinal agents may also be added to the bioabsorbable macromer compositions of the present disclosure. Medicinal agents which may be added include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and anti-anxiety agents, vitamin D preparations, hypoglycemic agents, antiulcer agents, hypnotics, antibiotics, antifungal agents, sedative agents, bronchodilator agents, antiviral agents and dysuric agents.

Where the bioabsorbable macromer composition is intended for delivery of a drug or protein, the amounts of the polymeric component possessing a lipid-like segment and optional second components can be adjusted to promote the initial retention of the drug or polymer in the bioabsorbable macromer composition and its subsequent release. Methods and means for making such adjustments will be readily apparent to those skilled in the art.

Imaging agents such as iodine or barium sulfate, or fluorine, can also be combined with the bioabsorbable macromer compositions of the present disclosure to allow visualization of the surgical area through the use of imaging equipment, including X-ray, MRI, and CAT scan.

Additionally, an enzyme may be added to the bioabsorbable macromer compositions of the present disclosure to increase their rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the bioabsorbable macromer composition of the present disclosure. Methods for incorporating enzymes into liposomes and/or microspheres are with the purview of those skilled in the art.

The bioabsorbable macromer compositions of the present disclosure can be used for a number of different human and animal medical applications including, but not limited to, wound closure (including surgical incisions and other wounds), adhesives for adhering medical devices (including implants) to tissue, sealants and void fillers, and embolic agents. Adhesives may be used to bind tissue together either as a replacement of, or as a supplement to, sutures, staples, tapes and/or bandages. Use of the disclosed bioabsorbable macromer composition can eliminate or substantially reduce the number of sutures normally required during current practices, and eliminate the subsequent need for removal of staples and certain types of sutures. The disclosed bioabsorbable macromer composition can thus be particularly suitable for use with delicate tissues where sutures, clamps or other conventional tissue closure mechanisms may cause further tissue damage.

Additional applications include use of the bioabsorbable macromer compositions as sealants for sealing tissues to prevent or control blood or other fluid leaks at suture or staple lines. In another embodiment, the bioabsorbable macromer compositions can be used to attach skin grafts and position tissue flaps during reconstructive surgery. In still another embodiment, the bioabsorbable macromer compositions can be used to close tissue flaps in periodontal surgery.

In other embodiments, especially where the bioabsorbable macromer composition of the present disclosure is to be utilized as an implant or a void filler or sealant to fill a defect in an animal's body, it may be advantageous to more precisely control the conditions and extent of cross-linking; thus, it may be desirable to partially cross-link the macromer composition prior to its use to fill a void in animal tissue. In such a case the bioabsorbable macromer composition of the present disclosure can be applied to the void or defect and allowed to set, thereby filling the void or defect.

To effectuate the joining of two tissue edges, the two edges are approximated, and the polymeric component, i.e., the polymeric component possessing a lipid-like segment, optionally endcapped with a functional group such as an isocyanate, may be applied alone or in combination with the optional second component. The component(s) crosslink rapidly, generally taking less than one minute. It is believed that a functional group such as an isocyanate groups of the polymeric component possessing a lipid-like segment may adhere to tissue by linking directly to amine groups present on the tissue surface. In this case the macromer composition of the present disclosure can be used as an adhesive to close a wound, including a surgical incision. The macromer composition of the present disclosure can thus be applied to the wound and allowed to set, thereby closing the wound.

The present disclosure is also directed to a method for using the bioabsorbable macromer composition of the present disclosure to adhere a medical device to tissue. In embodiments, depending on the composition of the medical device, a coating may be required on the medical device. In some cases such a coating can include the polymeric component of the bioabsorbable macromer composition of the present disclosure, or where utilized, the second component. In some aspects, the medical device includes an implant. Other medical devices include, but are not limited to, pacemakers, stents, shunts, and the like. Generally, for adhering a device to the surface of animal tissue, the polymeric component and/or macromer composition of the present disclosure can be applied to the device, the tissue surface, or both. The device, bioabsorbable macromer composition, and tissue surface are then brought into contact with each other and the bioabsorbable macromer composition is allowed to set, thereby adhering the device and surface to each other.

In some embodiments the polymeric component could be applied to tissue, the second component applied to a device, or vice-versa, and the two contacted with each other to form a bioabsorbable macromer composition adhering the device to tissue.

The present bioabsorbable macromer composition can also be used to prevent post surgical adhesions. In such an application, the bioabsorbable macromer composition is applied and cured as a layer on surfaces of internal tissues in order to prevent the formation of adhesions at a surgical site during the healing process. In addition to the formation of adhesion barriers, the composition of the present disclosure may be utilized to form implants such as gaskets, buttresses, or pledgets for implantation.

When used as a sealant, the bioabsorbable macromer composition of the present disclosure can be used in surgery to prevent or inhibit bleeding or fluid leakage both during and after a surgical procedure. It can also be applied to prevent air leaks associated with pulmonary surgery. The macromer composition may be applied directly to the desired area in at least an amount necessary to seal off any defect in the tissue and seal off any fluid or air movement.

Application of the bioabsorbable macromer composition, whether as an adhesive or sealant, with or without other additives, can be done by any conventional means. These include dripping, brushing, or other direct manipulation of the bioabsorbable macromer composition on the tissue surface, or spraying of the bioabsorbable macromer composition onto the surface. In open surgery, application by hand, forceps or the like is contemplated. In endoscopic surgery, the bioabsorbable macromer composition can be delivered through the cannula of a trocar, and spread at the site by any device known in the art.

In embodiments, the bioabsorbable macromer composition can be dispensed from a conventional adhesive dispenser, which can provide mixing of the polymeric and optional second components prior to the dispenser. Such dispensers are disclosed, for example, in U.S. Pat. Nos. 4,978,336, 4,361,055, 4,979,942, 4,359,049, 4,874,368, 5,368,563, and 6,527,749, the disclosures of each of which are incorporated by reference herein.

As noted above, the polymeric component possessing a lipid-like segment of the present disclosure may be utilized to form bioabsorbable macromer compositions useful as tissue adhesives and/or sealants. One advantage that may be realized by including a lipid segment in the polymeric compositions of the present disclosure is that the adhesive and/or sealant may be localized to target tissue by selection of an appropriate lipid segment, and potential negative effects which may arise with run-off of the adhesive and/or sealant may be avoided due to the enhanced affinity of the polymeric component for the target tissue as a result of the lipid segment. For example, a lipid segment may be selected to enhance adherence of the polymeric component to the intestinal mucosa, potentially enabling staple-free endoluminal anastomoses of the gastrointestinal tract. Adhesive/sealants formed of the polymeric compositions of the present disclosure may also be utilized to deliver bioactive agents to tissue, including to surgical sites to which they are applied, such as anastomoses, with greater precision due, in part, to the targeting of tissue provided by the lipid segment.

The present bioabsorbable macromer compositions have other advantageous properties. The bioabsorbable macromer compositions of the present disclosure are safe, possess enhanced adherence to tissue, are biodegradable, have enhanced hemostatic potential, have low cost, and are easy to prepare and use. By varying the selection of the components, the strength and elasticity of the bioabsorbable macromer composition can be controlled, as can the gelation time.

The bioabsorbable macromer compositions rapidly form a compliant gel matrix, which insures stationary positioning of tissue edges or implanted medical devices in the desired location and lowers overall required surgical/application time. The bioabsorbable macromer compositions form strong cohesive bonds. They exhibit excellent mechanical performance and strength, while retaining the necessary pliability to adhere living tissue. This strength and pliability allows a degree of movement of tissue without shifting the surgical tissue edge. Additionally, the bioabsorbable macromer compositions are biodegradable, allowing the degradation components to pass safely through the subject's body.

It will be understood that various modifications may be made to the embodiments disclosed herein. Therefore the above description should not be construed as limiting, but merely as exemplifications of typical embodiments. Those skilled in the art will envision other modifications within the scope and spirit of the claims appended hereto.

What is claimed is:

1. A bioabsorbable macromer composition of the formula selected from the group consisting of $$R_1\text{-}[A]_v\text{-}R_2\text{---}R_3 \quad (IV)$$

and $$R_3\text{---}R_2\text{-}[A]_v\text{-}R_1\text{-}[A]_v\text{-}R_2\text{---}R_3 \quad (V)$$

wherein $R_1$ comprises a lipid segment selected from the group consisting of phosphoryl choline, phosphatidyl choline, phosphatidyl ethanolamine, phosphatidyl inositol, phosphatidyl glycerol, phosphatidyl serine, phosphatidic acid, lysophosphatidyl choline, lysophosphatidyl ethanolamine, lysophosphatidyl glycerol, lysophosphatidyl serine, lysophosphatidic acid, PEG-phosphatidylethanolamine, PVP-phosphatidylethanolamine, sphingosine, aminosphingosine, and combinations thereof, $R_2$ comprises a polymer selected from the group consisting of polysaccharides and polyols, $R_3$ comprises a functional component selected from the group consisting of isocyanates, succinimides, aldehydes, and combinations thereof, A is a bioabsorbable group, and v is a number from about 1 to about 20.

2. A bioabsorbable macromer composition comprising:
a polymeric component of the formula $$R_3\text{---}R_2\text{-}[A]_v\text{-}R_1\text{-}[A]_v\text{-}R_2\text{---}R_3 \quad (V)$$

wherein $R_1$ comprises a lipid segment selected from the group consisting of phosphoryl choline, phosphatidyl choline, phosphatidyl ethanolamine, phosphatidyl inositol, phosphatidyl glycerol, phosphatidyl serine, phosphatidic acid, lysophosphatidyl choline, lysophosphatidyl ethanolamine, lysophosphatidyl glycerol, lysophosphatidyl serine, lysophosphatidic acid, PEG-phosphatidylethanolamine, PVP-phosphatidylethanolamine, sphingosine, aminosphingosine, and combinations thereof, $R_2$ comprises a polymer selected from the group consisting of polysaccharides and polyols, $R_3$ comprises a functional component selected from the group consisting of isocyanates, succinimides, aldehydes, and combinations thereof, A is a bioabsorbable group, and v is a number from about 1 to about 20; and
a second component possessing at least one group reactive with the functional component on the polymeric compound.

3. A bioabsorbable macromer composition as in claim 2, wherein $R_2$ comprises a polyol selected from the group consisting of polyethylene oxide, polyethylene glycol, polypropylene glycol, polyethylene oxide-polypropylene oxide copolymers, polyethylene glycol-adipate, polyethylene glycol-polypropylene glycol copolymers, and combinations thereof.

4. A bioabsorbable macromer composition as in claim 2, wherein $R_2$ comprises polyethylene glycol.

5. A bioabsorbable macromer composition as in claim 2, wherein $R_2$ comprises a polysaccharide selected from the group consisting of sorbitol, mannitol, sucrose, dextran, and cyclodextrin.

6. A bioabsorbable macromer composition as in claim 2, wherein the bioabsorbable group is selected from the group consisting of lactic acid, glycolic acid, glycolide, lactide, c-caprolactone, trimethylene carbonate, 1,4-dioxane-2-one, 1,3-dioxane-2-one, succinnic acid, adipic acid, sebacic acid, malonic acid, glutaric acid, azelaic acid, ethyl dichlorophosphate, sebacic acid anhydride, azelaic acid anhydride, and combinations thereof.

7. A bioabsorbable macromer composition as in claim 2, wherein the bioabsorbable group is selected from the group consisting of lactide, glycolide, e-caprolactone, p-dioxanone, trimethylene carbonate, and combinations thereof.

8. A bioabsorbable macromer composition as in claim 2, wherein v is a number from about 2 to about 6.

9. A bioabsorbable macromer composition as in claim 2, wherein the isocyanate group is selected from the group consisting of 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenyl isocyanate), tetramethylxylylene diisocyanate, tetramethylene diisocyanate, hexamethylene diisocyanate, lysine diisocyanate, 2-methylpentane-1,5-diisocyanate, 3-methylpentane-1,5-diisocyanate, 2,2,4-trimethylhexamethylene diisocyanate, isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate, and combinations thereof.

10. A bioabsorbable macromer composition as in claim 2, wherein the second component possesses at least one isocyanate-reactive group selected from the group consisting of at least one hydroxy group, at least one amine group, at least one sulfhydryl group, and combinations thereof.

11. A bioabsorbable macromer composition as in claim 10, wherein the second component possessing at least one hydroxy group is selected from the group consisting of water, polyether-based polyols, polycaprolactone-based polyols, and polyhydric alcohols, disaccharides, and combinations thereof.

12. A bioabsorbable macromer composition as in claim 10, wherein the second component possessing at least one amine group is selected from the group consisting of bis(3-aminopropyl)amine, spermine, polyetheramines, trilysine, polylysine, polyarginine, albumin, ethylenediamine, N-ethylethylenediamine, N,N'-diethylethylenediamine, butane-1,4-diamine, pentane-1,5-diamine, hexane-1,6-diamine, phenylene diamine, ethanolamine, N-ethylethanolamine, triethylenediamine, N-methylmorpholine, pentamethyl diethylenetriamine, dimethylcyclohexylamine, tetramethylethylenediamine, 1-methyl-4-dimethylaminoethyl-piperazine, 3-methoxy-N-dimethyl-propylamine, N-ethylmorpholine, diethylethanolamine, N-cocomorpholine, N,N-dimethyl-N'N-dimethylisopropyl-propylene diamine, N,N-diethyl-3-diethyl aminopropylamine, dimethyl-benzyl amine, and combinations thereof.

13. A bioabsorbable macromer composition as in claim 10, wherein the second component possessing at least one amine group comprises a diamine of the formula $$NH_2\text{---}R_4\text{---}NH_2 \quad (VI)$$

wherein $R_4$ comprises a polymer selected from the group consisting of polysaccharides and polyols.

14. A bioabsorbable macromer composition as in claim 10, wherein the second component possessing at least one sulfhydryl group is selected from the group consisting of thiolated gelatin, thiolated collagen, PEG-thiols, pentaerythritol tetrakis(2-mercaptoacetate), pentaerythritol tetrakis(3-mercaptopropionate), trimethylolpropane tris(2-mercaptoacetate), trimethylolpropane tris(2-mercaptopropionate), and combinations thereof.

15. A method for closing a wound comprising:
applying the bioabsorbable macromer composition of claim 2 to said wound; and
allowing the bioabsorbable macromer composition to set thereby closing said wound.

16. The method of claim 15 wherein the wound is a surgical incision.

17. A method for filling a void in animal tissue comprising:
applying the bioabsorbable macromer composition of claim 2 to said void; and
allowing the bioabsorbable macromer composition to set thereby filling said void.

18. A method for adhering a medical device to a surface of animal tissue comprising the steps of:
applying the bioabsorbable macromer composition of claim 2 to said device, said surface or both;
bringing the device, bioabsorbable macromer composition and surface into contact with each other; and
allowing the bioabsorbable macromer composition to set thereby adhering the device and surface to each other.

19. The method of claim 18, wherein said medical device is an implant.

* * * * *